(12) United States Patent
Kuo et al.

(10) Patent No.: US 8,529,936 B2
(45) Date of Patent: Sep. 10, 2013

(54) LONG TERM DRUG DELIVERY DEVICES WITH POLYURETHANE BASED POLYMERS AND THEIR MANUFACTURE

(71) Applicant: Endo Pharmaceuticals Solutions Inc., Chadds Ford, PA (US)

(72) Inventors: Sheng-hung Kuo, Plainsboro, NJ (US); Petr Kuzma, Princeton, NJ (US)

(73) Assignee: Endo Pharmaceuticals Solutions Inc., Malvern, PA (US)

( * ) Notice: Subject to any disclaimer, the term of this patent is extended or adjusted under 35 U.S.C. 154(b) by 0 days.

(21) Appl. No.: 13/693,659

(22) Filed: Dec. 4, 2012

(65) Prior Publication Data

US 2013/0096496 A1 Apr. 18, 2013

Related U.S. Application Data

(63) Continuation of application No. 12/873,130, filed on Aug. 31, 2010, now Pat. No. 8,357,389, which is a continuation of application No. 10/915,625, filed on Aug. 10, 2004, now Pat. No. 7,842,303.

(60) Provisional application No. 60/494,132, filed on Aug. 11, 2003.

(51) Int. Cl.
*A61F 2/00* (2006.01)
*A61L 27/54* (2006.01)

(52) U.S. Cl.
CPC ..................................... *A61L 27/54* (2013.01)
USPC ........................................ 424/423; 604/890.1

(58) Field of Classification Search
None
See application file for complete search history.

(56) References Cited

U.S. PATENT DOCUMENTS

| | | | |
|---|---|---|---|
| 3,948,254 A | 4/1976 | Zaffaroni |
| 3,975,350 A | 8/1976 | Hudgin |
| 3,993,073 A | 11/1976 | Zaffaroni |
| 4,131,604 A | 12/1978 | Szycher |
| 4,136,145 A | 1/1979 | Fuchs |
| 4,207,809 A | 6/1980 | Brill |
| 4,207,890 A | 6/1980 | Mamajek |
| 4,386,039 A | 5/1983 | Szycher |

(Continued)

FOREIGN PATENT DOCUMENTS

| | | |
|---|---|---|
| EP | 0200224 A2 | 11/1986 |
| EP | 0241178 A1 | 10/1987 |

(Continued)

OTHER PUBLICATIONS

U.S. Appl. No. 12/907,717, Notice of Allowance mailed Jun. 8, 2012.

(Continued)

*Primary Examiner* — Bethany Barham
(74) *Attorney, Agent, or Firm* — RatnerPrestia

(57) ABSTRACT

This invention is related to the use of polyurethane based polymer as a drug delivery device to deliver biologically active compounds at a constant rate for an extended period of time and methods of manufactures thereof. The device is very biocompatible and biostable, and is useful as an implant in patients (humans and animals) for the delivery of appropriate bioactive substances to tissues or organs. The drug delivery device for releasing one or more drugs at controlled rates for an extended period of time to produce local or systemic pharmacological effects comprises:

1. a reservoir, said reservoir comprising;
2. at least one active ingredient; and, optionally,
3. at least one pharmaceutically acceptable carrier;

a polyurethane based polymer completely surrounding the reservoir.

32 Claims, 7 Drawing Sheets

(56) References Cited

U.S. PATENT DOCUMENTS

| | | | |
|---|---|---|---|
| 4,469,671 | A | 9/1984 | Zimmerman |
| 4,523,005 | A | 6/1985 | Szycher |
| 4,743,673 | A | 5/1988 | Johnston |
| 4,751,133 | A | 6/1988 | Szycher |
| 4,933,182 | A | 6/1990 | Higashi |
| 5,035,891 | A | 7/1991 | Runkel |
| 5,207,705 | A | 5/1993 | Trudell |
| 5,254,662 | A | 10/1993 | Szycher |
| 5,266,325 | A | 11/1993 | Kuzma |
| 5,292,515 | A | 3/1994 | Moro |
| 5,354,835 | A | 10/1994 | Blair |
| 5,626,862 | A | 5/1997 | Brem |
| 5,629,008 | A | 5/1997 | Lee |
| 5,728,396 | A | 3/1998 | Peery |
| 5,756,632 | A | 5/1998 | Ward |
| 5,789,411 | A | 8/1998 | Gooberman |
| 5,980,927 | A | 11/1999 | Nelson |
| 6,113,938 | A | 9/2000 | Chen |
| 6,287,295 | B1 | 9/2001 | Chen |
| 6,313,254 | B1 | 11/2001 | Meijs |
| 6,375,978 | B1 | 4/2002 | Kleiner |
| 7,067,116 | B1 | 6/2006 | Bess |
| 7,648,712 | B2 | 1/2010 | Bess |
| 2001/0006677 | A1 | 7/2001 | McGinity |
| 2002/0028857 | A1 | 3/2002 | Holy |
| 2003/0153983 | A1 | 8/2003 | Miller |
| 2003/0170305 | A1 | 9/2003 | O'Neil |
| 2004/0002729 | A1 | 1/2004 | Zamore |
| 2005/0037078 | A1 | 2/2005 | Kuo |
| 2005/0202371 | A1 | 9/2005 | McGuire |
| 2006/0204540 | A1 | 9/2006 | Kuzma |
| 2006/0204559 | A1 | 9/2006 | Bess |
| 2008/0004260 | A1 | 1/2008 | Singh |
| 2009/0098182 | A1 | 4/2009 | Kuzma |
| 2009/0208540 | A1 | 8/2009 | Kuzma |
| 2010/0080835 | A1 | 4/2010 | Kuzma |
| 2010/0203104 | A1 | 8/2010 | De Graaff |
| 2011/0059147 | A1 | 3/2011 | Kuo |
| 2011/0184376 | A1 | 7/2011 | Kuzma |

FOREIGN PATENT DOCUMENTS

| | | |
|---|---|---|
| EP | 1660034 A2 | 5/2006 |
| EP | 1982695 A2 | 10/2008 |
| JP | 10076016 A | 3/1998 |
| WO | WO-0143726 A1 | 6/2001 |
| WO | WO-0170194 A1 | 9/2001 |
| WO | WO-2005013936 A2 | 2/2005 |
| WO | WO-2006078320 A2 | 7/2006 |
| WO | WO-2006099288 A3 | 9/2006 |
| WO | WO-2008070118 A1 | 6/2008 |
| WO | WO-2009158415 A1 | 12/2009 |
| WO | WO-2010039641 A2 | 4/2010 |
| WO | WO-2010039717 A1 | 4/2010 |
| WO | WO-2010039722 A1 | 4/2010 |

OTHER PUBLICATIONS

U.S. Appl. No. 12/907,717, Notice of Allowance mailed Aug. 29, 2012.
U.S. Appl. No. 12/351,617, Non Final Office Action mailed Dec. 8, 2010.
U.S. Appl. No. 10/915,625, Notice of Allowance mailed Jul. 6, 2010.
U.S. Appl. No. 12/242,497, Notice of Allowance mailed Sep. 16, 2010.
U.S. Appl. No. 12/873,130, Non Final Office Action mailed Oct. 4, 2011.
U.S. Appl. No. 12/242,497, Non Final Office Action mailed Feb. 3, 2010.
U.S. Appl. No. 12/873,130, Notice of Allowance mailed Sep. 25, 2012, 10 pgs.
U.S. Appl. No. 12/569,558, Non Final Office Action mailed Nov. 8, 2011.
U.S. Appl. No. 10/915,625, Final Office Action mailed Mar. 16, 2009.
U.S. Appl. No. 12/907,717, Non Final Office Action mailed Feb. 27, 2012, 10 pgs.
U.S. Appl. No. 10/915,625, Final Office Action mailed Mar. 31, 2010.
U.S. Appl. No. 12/915,625, Non Final Office Action mailed Sep. 29, 2009.
U.S. Appl. No. 12/873,130, Notice of Allowance mailed Feb. 27, 2012, 17 pgs.
U.S. Appl. No. 10/915,625, Non Final Office Action mailed Sep. 7, 2007.
Chinese Application Serial No. 200480029342.0, Chinese Office Action dated Sep. 21, 2007.
Chinese Application Serial No. 200480029342.0, Chinese Office Action dated Nov. 27, 2009.
European Application Serial No. 08010973, European Search Report dated Apr. 27, 2010.
Indian Application Serial No. 282/MUMNP/2006, First Examination Report.
International Application Serial No. PCT/US2009/059012, International Search Report and Written Opinion mailed Dec. 17, 2009.
International Application Serial No. PCT/US2009/058810, International Search Report and Written Opinion dated Feb. 3, 2010.
International Application Serial No. PCT/US2009/058571, International Search Report and Written Opinion dated May 31, 2010.
International Application Serial No. PCT/US2009/058578, International Search Report and Written Opinion mailed Feb. 2, 2010.
International Application Serial No. PCT/US2009/058801, International Search Report and Written Opinion dated Feb. 5, 2010.
Japanese Application Serial No. 2011-031294, Notice of Reason for Refusal dated Oct. 11, 2011.
Mexican Application Serial No. PA/a/2006-001612, Mexican Office Action dated Jul. 25, 2008.
Mexican Application Serial No. PA/a/2006-001612, Mexican Office Action dated Jan. 20, 2009.
Mexican Application Serial No. PA/a/2006-001612, Mexican Office Action dated Jan. 18, 2010.
Mexican Application Serial No. PA/a/2006-001612, Mexican Office Action dated Jul. 22, 2009.
"Remington: The Science and Practice of Pharmacy", A.R. Genaro Editor, Mack Publishing (1995).
Grigorieva, M., "Polyurethane Composites for Medical Applications", Advances in Plastics Technology, International Conference, 5th, Katowice, Poland (Nov. 4-6, 2003) Abstract only, 4/1-4/5.
Hsu, "Plasma-Induced Graft Polymerization of L-Lactide on Polyurethane", 24th Annual Mtg. Soc. Biomat, San Diego, CA (Apr. 22-26, 1998).
Radebough, "Remington: The Science and Practice of Pharmacy", Remington's Pharmaceutical Sciences, 19th Edition, vol. 2, Mack Publishing Co. Easton, PA (1995), 1457.
Ulrich, Henri, "PolyUrethanes", Encyclopedia of Polymer Science and Technology, John Wiley & Sons (2002).
Zondervan, "Design of a Polyurethane Membrane for the Encapsulation of Islets of Langerhans", Biomaterials, vol. 13, No. 3 (1992), 134-144.
Second Office Action for Chinese Application No. 200980142114.7 dated Feb. 28, 2013, with English language translation.
Office Action issued by the Ukraine Patent Office for Application No. a201105431 dated Mar. 21, 2013, with English language translation.
Office Action issued by the Patent Office of the Russian Federation for Application No. 2011117328 dated Apr. 15, 2013.
Office Action Issued for Japanese Application No. 2011-031294 Dated May 28, 2013.
State of Israel Registrar of Patents, Notification of Defects in Patent Application No. 211593, dated May 26, 2013.

LONG TERM DRUG DELIVERY DEVICES WITH POLYURETHANE BASED POLYMERS AND THEIR MANUFACTURE

CROSS-REFERENCE TO RELATED APPLICATION(S)

This application is a continuation of U.S. patent application Ser. No. 12/873,130, filed Aug. 31, 2010, which is a continuation of U.S. patent application Ser. No. 10/915,625, filed Aug. 10, 2004, which claims priority from U.S. Provisional Patent Application No. 60/494,132, filed Aug. 11, 2003. The contents of these applications are incorporated by reference herein in their entireties and for all purposes.

FIELD OF INVENTION

The present invention relates to the field of drug delivery devices and more specifically implantable drug deliver)/devices made of polyurethane based polymers.

BACKGROUND OF THE INVENTION

Due to its excellent biocompatibility, biostability and physical properties, polyurethane or polyurethane-containing polymers have been used to fabricate a large number of implantable devices, including pacemaker leads, artificial hearts, heart valves, stent coverings, artificial tendons, arteries and veins. See e.g., www.polymertech.com, wvvw.cardiotech-inc.com, and www.thermedicsinc.com. Also see Hsu et al., Soc. Biomaterials Trans., April 1998.

Known in the art is U.S. Pat. No. 3,975,350 which discloses the use of polyurethanes to make implants containing pharmaceutically active agents. This patent discloses that the active agents are mixed with the polyurethane polymer prior to being cast (or shaped) into a number of forms, including tubes, rods, films, etc.

Also known is U.S. Pat. No. 3,993,073 which discloses a delivery device for the controlled and continuous administration of a drug to a body site. The device disclosed therein comprises a reservoir containing a dissolved drug surrounded by a shaped wall which is insoluble in body fluid.

U.S. Pat. No. 3,948,254 discloses a drug delivery device for the administration of a drug. The drug is contained within a reservoir and the device comprises pores filled with a liquid which is permeable to the passage of the drug.

The inventors are not aware of any prior art polyurethane based drug delivery devices which can contain a drug in a solid form and which does not require a liquid medium or carrier for the diffusion of the drug at a zero order rate.

SUMMARY OF THE INVENTION

It is an object of the present invention to provide polyurethane based long term drug delivery devices.

It is a further object of the present invention to provide biocompatible and biostable polyurethane based devices for the delivery of drugs or other compounds in a living organism.

This is accomplished through a drug delivery device for releasing one or more drugs at controlled rates for an extended period of time to produce local or systemic pharmacological effects, said drug delivery device having a reservoir comprising:
  a) a polyurethane based polymer completely surrounding the reservoir;
  b) at least one active ingredient; and, optionally,
  c) at least one pharmaceutically acceptable carrier;

Preferably, the drug delivery device has a cylindrically shaped reservoir.

Preferably also, the polyurethane based polymer is selected from the group consisting of: thermoplastic polyurethane, and thermoset polyurethane. Even more preferably, the thermoplastic polyurethane is made of macrodials, diisocyanates, difunctional chain extenders or mixtures thereof.

Preferably, the thermoset polyurethane is made of multifunctional polyols, isocyanates, chain extenders or mixtures thereof.

Preferably also, the thermoset polyurethane comprises a polymer chain and cross-linking members, said thermoset polyurethane contains unsaturated bonds in the polymer chains and appropriate crosslinkers and/or initiators as cross-linking members.

Preferably, the drug delivery device is made of polyurethane which comprises functional groups selected from hydrophilic pendant groups and hydrophobic pendant groups. More preferably, the hydrophilic pendant groups are selected from ionic, carboxyl, ether, hydroxyl groups and mixtures thereof. Even more preferably, the hydrophobic pendant groups are selected from alkyl and siloxane groups and mixtures thereof.

Another object of the present invention is a process of manufacturing a drug delivery device, said process comprising:
  a) precision extrusion or injection molding step to produce a hollow tube made of thermoplastic polyurethane with two open ends with desired physical dimensions;
  b) sealing one of the open ends of the hollow tube;
  c) loading a reservoir containing a desired formulation containing actives and, optionally, carriers or filling a reservoir with pre-fabricated pellets;
  d) sealing the second open end of the hollow tube; and
  e) conditioning and priming of the drug delivery devices to achieve the desired delivery rates for the actives.

Preferably, the sealing steps may be carried out by using pre-fabricated plugs which are inserted on the open ends of the hollow tube with heat or solvent or by applying heat or solvent while sealing or any other means to seal the ends, preferably permanently.

Yet another object of the present invention is a process of manufacturing drug delivery devices made with thermoset polyurethanes, said process comprising:
  a) precision reaction injection molding or spin casting a hollow tube having two open ends;
  b) curing the hollow tube;
  c) sealing one end of the hollow tube;
  d) loading a reservoir containing a desired formulation containing actives and, optionally, carriers or filling a reservoir with pre-fabricated pellets;
  e) sealing the second end of the hollow tube; and
  f) conditioning and priming of the drug delivery devices to achieve the desired delivery rates for the actives.

Yet another object of the present invention is a process of manufacturing drug delivery devices made with thermoset polyurethanes, said process comprising:
  a) precision reaction injection molding or spin casting a hollow tube having one open end;
  b) curing the hollow tube;
  c) loading a reservoir containing a desired formulation containing actives and, optionally, carriers or filling a reservoir with pre-fabricated pellets;
  d) sealing the open end of the hollow tube; and
  e) conditioning and priming of the drug delivery devices to achieve the desired delivery rates for the actives.

Another object of the present invention is a process of manufacturing drug delivery devices made with thermoset polyurethanes, wherein the production of the hollow tube and sealing of an open end, is done with an appropriate light-initiated and/or heat-initiated thermoset polyurethane formulation and initiating and curing the light-initiated and/or heat-initiated thermoset polyurethane formulation with light and/or heat or any other means to seal the ends, preferably permanently.

Also another object of the present invention involves a process of manufacturing drug delivery devices made with thermoset polyurethanes, wherein the sealing of an open end, is done by inserting a pre-fabricated end plug at the open end of the hollow tube by suitable means, for example, as described in U.S. Pat. No. 5,292,515. Such suitable means are preferably pharmaceutically acceptable adhesives.

Yet another object of the invention is a process of manufacturing drug delivery devices made with thermoset polyurethanes, wherein the sealing of an open end, is done by inserting a pre-fabricated end plug at the open end of the hollow tube and by applying an appropriate light-initiated and/or heat-initiated thermoset polyurethane formulation on interface between the pre-fabricated end plug and the open end and initiating and curing with light and/or heat or any other means to seal the ends, preferably permanently.

In one instance there is provided a drug delivery device for releasing one or more drugs at controlled rates for an extended period of time to produce local or systemic pharmacological effects, said drug delivery device having a reservoir comprising:
  i. at least one active ingredient; and, optionally,
  ii. at least one pharmaceutically acceptable carrier; and
  iii. a polyurethane based polymer completely surrounding the reservoir.

Preferably the drug delivery device has a cylindrically shaped reservoir.

Preferably, the polyurethane based polymer is selected from the group comprising: thermoplastic polyurethane, and thermoset polyurethane. More preferably, the thermoplastic polyurethane is made of macrodials, diisocyanates, difunctional chain extenders or mixtures thereof. Also more preferably, the thermoset polyurethane is made of multifunctional polyols, isocyanates, chain extenders or mixtures thereof.

Even more preferably, the thermoset polyurethane comprises a polymer chain and cross-linking members, said thermoset polyurethane contains unsaturated bonds in the polymer chains and appropriate crosslinkers and/or initiators as cross-linking members.

Preferably, the polyurethane comprises functional groups selected from hydrophilic pendant groups and hydrophobic pendant groups. More preferably, the hydrophilic pendant groups are selected from ionic, carboxyl, ether, hydroxyl groups and mixtures thereof. Also preferably, the hydrophobic pendant groups are selected from alkyl, siloxane groups and mixtures thereof.

In one instance there is provided for a process of manufacturing drug delivery devices made with thermoplastic polyurethanes, said process comprising:
  a) precision extrusion or injection molding step to produce a hollow tube made of thermoplastic polyurethane with two open ends with desired physical dimensions;
  b) sealing one of the open ends of the hollow tube;
  c) loading a reservoir containing a desired formulation containing actives and, optionally, carriers or filling a reservoir with pre-fabricated pellets;
  d) sealing the second open end of the hollow tube;
  e) conditioning and priming of the drug delivery devices to achieve the desired delivery rates for the actives.

Preferably, the sealing steps may be carried out by using pre-fabricated plugs which are inserted on the open ends of the hollow tube with heat or solvent or by applying heat or solvent while sealing or any other means to seal the ends, preferably permanently.

In one instance there is provided for a process of manufacturing drug delivery devices made with thermoset polyurethanes, said process comprising:
  a) precision reaction injection molding or spin casting a hollow tube having two open ends;
  b) curing the hollow tube;
  c) sealing one end of the hollow tube;
  d) loading a reservoir containing a desired formulation containing actives and, optionally, carriers or filling a reservoir with pre-fabricated pellets;
  e) sealing the second end of the hollow tube; and
  f) conditioning and priming of the drug delivery devices to achieve the desired delivery rates for the actives.

In another instance there is provided for a process of manufacturing drug delivery devices made with thermoset polyurethanes, said process comprising:
  a) precision reaction injection molding or spin casting a hollow tube having one open end;
  b) curing the hollow tube;
  c) loading a reservoir containing a desired formulation containing actives and, optionally, carriers or filling a reservoir with pre-fabricated pellets;
  d) sealing the open end of the hollow tube; and
  e) conditioning and priming of the drug delivery devices to achieve the desired delivery rates for the actives.

Preferably, the production of the hollow tube and the sealing of an open end are done with an appropriate light-initiated and/or heat-initiated thermoset polyurethane formulation and initiating and curing the light-initiated and/or heat-initiated thermoset polyurethane formulation with light and/or heat or any other means to seal the ends, preferably permanently.

More preferably, the sealing of an open end, is done by inserting a pre-fabricated end plug at the open end of the hollow tube by suitable means, for example, as described in U.S. Pat. No. 5,292,515. Such suitable means are preferably pharmaceutically acceptable adhesives. Even more preferably, the sealing of an open end, is done by inserting a pre-fabricated end plug at the open end of the hollow tube and by applying an appropriate light-initiated and/or heat-initiated thermoset polyurethane formulation on interface between the pre-fabricated end plug and the open end and initiating and curing with light and/or heat or any other means to seal the ends, preferably permanently.

DETAILED DESCRIPTION OF THE FIGURES

DETAILED DESCRIPTION OF THE INVENTION

To take the advantage of the excellent properties of polyurethane based polymers, this invention uses polyurethane based polymers as drug delivery devices for releasing drugs at controlled rates for an extended period of time to produce local or systemic pharmacological effects. The drug delivery device is preferably comprised of a cylindrically shaped reservoir surrounded by polyurethane based polymer through which controls the delivery rate of the drug inside the reservoir. The reservoir is comprised of active ingredients and, optionally, pharmaceutically acceptable carriers. The carriers are formulated to facilitate the diffusion of the active ingredients through the polymer and to ensure the stability of the drugs inside the reservoir.

The current invention provides a drug delivery device that can achieve the following objectives: a controlled release rate (zero order release rate) to maximize therapeutic effects and minimize unwanted side effects; an easy way to retrieve the device if it is necessary to end the treatment; an increase in bioavailability with less variation in absorption and no first pass metabolism.

The release rate of the drug is governed by the Fick's Law of Diffusion as applied to a cylindrically shaped reservoir device (cartridge). The following equation describes the relationship between different parameters:

$$\frac{dM}{dt} = \frac{2\pi h \, p \, \Delta C}{\ln(r_o/r_i)}$$

where:
- dM/dt: drug release rate;
- h: length of filled portion of device;
- ΔC: concentration gradient across the reservoir wall;
- $r_o/r_i$: ratio of outside to inside radii of device; and
- p: permeability coefficient of the polymer used.

The permeability coefficient is primarily regulated by the hydrophilicity/hydrophobicity of the polymer, the structure of the polymer, and the interaction of drug and the polymer. Once the polymer and the active ingredient are selected, p will be a constant, h, $r_o$, and $r_i$ are fixed and kept constant once the cylindrically shaped device is produced. ΔC is maintained constant by the carriers inside the reservoir.

To keep the geometry of the device as precise as possible, the preferably cylindrically shaped device can be manufactured through precision extrusion or precision molding process for thermoplastic polyurethane polymers, and reaction injection molding or spin casting process for thermosetting polyurethane polymers.

The cartridge can be made with either one end closed or both ends open. The open end can be plugged with pre-manufactured end plug to ensure a smooth end and a solid seal. The solid actives and carriers can be compressed into pellet form to maximize the loading of the actives.

To identify the location of the implant, radiopaque material can be incorporated into the delivery device by inserting it into the reservoir or by making it into end plug to be used to seal the cartridge.

Once the cartridges are sealed on both ends with filled reservoir, they are conditioned and primed for an appropriate period of time to ensure a constant delivery rate.

The conditioning of the drug delivery devices involves the loading of the actives (drug) into the polyurethane based polymer which surrounds the reservoir. The priming is done to stop the loading of the drug into the polyurethane based polymer and thus prevent loss of the active before the actual use of the implant. The conditions used for the conditioning and priming step depend on the active, the temperature and the medium in which they are carried out. The conditions for the conditioning and priming may be the same in some instances.

The conditioning and priming step in the process of the preparation of the drug delivery devices is done to obtain a determined rate of release of a specific drug. The conditioning and priming step of the implant containing a hydrophilic drug is preferably carried out in an aqueous medium, more preferably in a saline solution. The conditioning and priming step of a drug delivery device comprising a hydrophobic drug is usually carried out in a hydrophobic medium such as an oil based medium. The conditioning and priming steps are carried out by controlling three specific factors namely the temperature, the medium and the period of time.

A person skilled in the art would understand that the conditioning and priming step of the drug delivery device will be affected by the medium in which the device is placed. As mentioned previously, a hydrophilic drug would be preferably conditioned and primed in an aqueous solution and more preferably, in a saline solution. For example, Histrelin and Naltrexone implants have been conditioned and primed in saline solution, more specifically, conditioned in saline solution of 0.9% sodium content and primed in saline solution of 1.8% sodium chloride content.

The temperature used to condition and prime the drug delivery device may vary across a wide range of temperatures but, in some instances 37° C., has been preferably used.

The time period used for the conditioning and priming of the drug delivery devices may vary from a single day to several weeks depending on the release rate desired for the specific implant or drug.

A person skilled in the art will understand the steps of conditioning and priming the implants is to optimize the rate of release of the drug contained within the implant. As such, a shorter time period spent on the conditioning and the priming of a drug delivery device results in a lower rate of release of the drug compared to a similar drug delivery device which has undergone a longer conditioning and priming step.

The temperature in the conditioning and priming step will also affect the rate of release in that a lower temperature results in a lower rate of release of the drug contained in the drug delivery device when compared to a similar drug delivery device which has undergone a treatment at a higher temperature.

Similarly, in the case of aqueous solutions, which are in some cases preferably saline solutions, the sodium chloride content of the solution will also determine what type of rate of release will be obtained for the drug delivery device. More specifically, a lower content of sodium chloride would result in a higher rate of release of drug when compared to a drug delivery device which has undergone a conditioning and priming step where the sodium chloride content was higher.

The same conditions apply for hydrophobic drugs where the main difference in the conditioning and priming step would be that the conditioning and priming medium be hydrophobic medium, more specifically an oil based medium.

The drug (actives) that can be delivered include drugs that can act on the central nervous system, psychic energizers, tranquilizers, anti-convulsants, muscle relaxants, anti-parkinson, analgesic, anti-inflammatory, anesthetic, antispasmodic, muscle contractants, anti-microbials, anti-malarials, hormonal agents, sympathomimetic, cardiovascular, diuretics, anti-parasitic and the like.

The current invention focuses on the application of polyurethane based polymers, thermoplastics or thermosets, to the creation of implantable drug devices to deliver biologically active compounds at controlled rates for prolonged period of time. Polyurethane polymers are preferably made into cylindrical hollow tubes with one or two open ends through extrusion, (reaction) injection molding, compression molding, or spin-casting (see e.g. U.S. Pat. Nos. 5,266,325 and 5,292,515), depending on the type of polyurethane used.

Thermoplastic polyurethane can be processed through extrusion, injection molding, or compression molding. Thermoset polyurethane can be processed through reaction injection molding, compression molding, or spin-casting. The dimensions of the cylindrical hollow tube are very critical and need to be as precise as possible.

Polyurethane based polymers are synthesized from multifunctional polyols, isocyanates and chain extenders. The characteristics of each polyurethane can be attributed to its structure.

Thermoplastic polyurethanes are made of macrodials, diisocyanates, and difunctional chain extenders (e.g. U.S. Pat. Nos. 4,523,005 and 5,254,662). Macrodials make up the soft domains. Diisocyanates and chain extenders make up the hard domains. The hard domains serve as physical crosslinking sites for the polymers. Varying the ratio of these two domains can alter the physical characteristics of the polyurethanes.

Thermoset polyurethanes can be made of multifunctional (greater than difunctional) polyols and/or isocyanates and/or chain extenders (e.g. U.S. Pat. Nos. 4,386,039 and 4,131,604). Thermoset polyurethanes can also be made by introducing unsaturated bonds in the polymer chains and appropriate crosslinkers and/or initiators to do the chemical crosslinking (e.g. U.S. Pat. No. 4,751,133). By controlling the amounts of crosslinking sites and how they are distributed, the release rates of the actives can be controlled.

Different functional groups can be introduced into the polyurethane polymer chains through the modification of the backbones of polyols depending on the properties desired. When the device is used for the delivery of water soluble drugs, hydrophilic pendant groups such as ionic, carboxyl, ether, and hydroxy groups are incorporated into the polyols to increase the hydrophilicity of the polymer (e.g. U.S. Pat. Nos. 4,743,673 and 5,354,835). When the device is used for the delivery of hydrophobic drugs, hydrophobic pendant groups such as alkyl, siloxane groups are incorporated into the polyols to increase the hydrophobicity of the polymer (e.g. U.S. Pat. No. 6,313,254). The release rates of the actives can also be controlled by the hydrophilicity/hydrophobicity of the polyurethane polymers.

Once the appropriate polyurethane polymer is chosen, the next step is to determine the best method to fabricate the cylindrically shaped implants.

Figure 1:
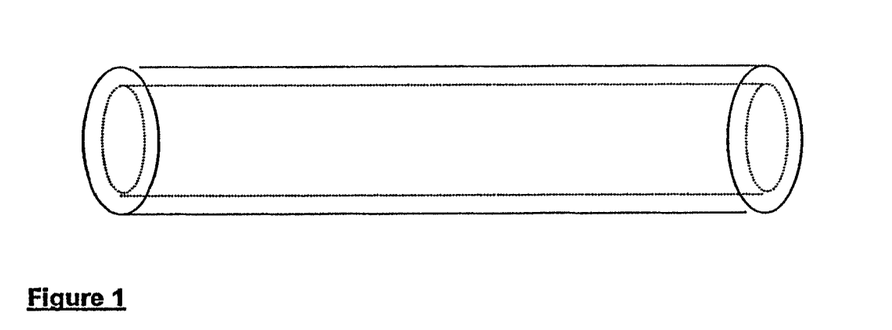
FIG. 1 is a side view of an implant with two open ends as used in the present invention.
Figure 2:
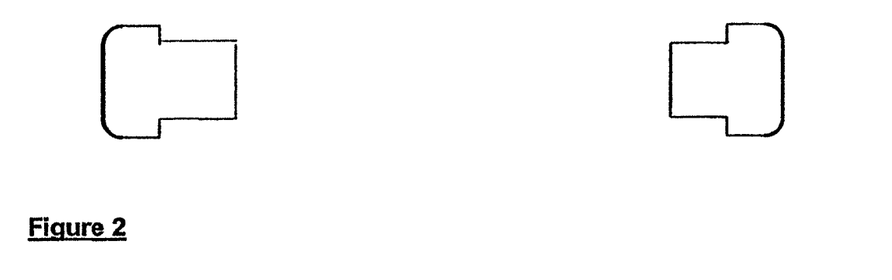
FIG. 2 is a side view of the pre-fabricated end plugs used to plug the implants according to the present invention.

For thermoplastic polyurethanes, precision extrusion and injection molding are the preferred choices to produce two open-end hollow tubes (see FIG. 1) with consistent physical dimensions. The reservoir can be loaded freely with appropriate formulations containing actives and carriers or filled with pre-fabricated pellets to maximize the loading of the actives. One open end needs to be sealed first before the loading of the formulation into the hollow tube. To seal the two open ends, two pre-fabricated end plugs (see FIG. 2) are used. The sealing step can be accomplished through the application of heat or solvent or any other means to seal the ends, preferably permanently.

Figure 3:
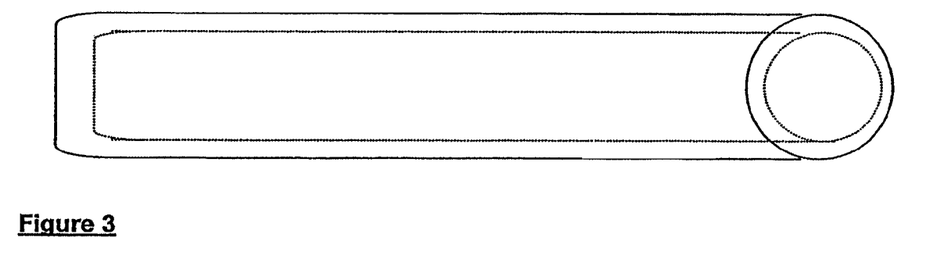
FIG. 3 is a side view of an implant with one open end as used in the present invention.

For thermoset polyurethanes, precision reaction injection molding or spin casting is the preferred choice depending on the curing mechanism. Reaction injection molding is used if the curing mechanism is carried out through heat and spin casting is used if the curing mechanism is carried out through light and/or heat. Preferably, hollow tubes with one open end (see FIG. 3) are made by spin casting. Preferably, hollow tubes with two open ends are made by reaction injection molding. The reservoir can be loaded in the same way as the thermoplastic polyurethanes.

Preferably, to seal an open end, an appropriate light-initiated and/or heat-initiated thermoset polyurethane formulation is used to fill the open end and this is cured with light and/or heat. More preferably, a pre-fabricated end plug can also be used to seal the open end by applying an appropriate light-initiated and/or heat-initiated thermoset polyurethane formulation on to the interface between the pre-fabricated end plug and the open end and cured it with the light and/or heat or any other means to seal the ends, preferably permanently.

The final process involves the conditioning and priming of the implants to achieve the delivery rates required for the actives. Depending upon the types of active ingredient, hydrophilic or hydrophobic, the appropriate conditioning and priming media will be chosen. Water based media are preferred for hydrophilic actives and oil based media are preferred for hydrophobic actives.

As a person skilled in the art would readily know many changes can be made to the preferred embodiments of the invention without departing from the scope thereof. It is intended that all matter contained herein be considered illustrative of the invention and not it a limiting sense.

EXAMPLE 1

Tecophilic polyurethane polymer tubes are supplied by Thermedics Polymer Products and manufactured through a precision extrusion process. Tecophilic polyurethane is a family of aliphatic polyether-based thermoplastic polyurethane which can be formulated to different equilibrium water content contents of up to 150% of the weight of dry resin. Extrusion grade formulations are designed to provide maximum physical properties of thermoformed tubing or other components.

The physical data for the polymers is provided below as made available by Thermedics Polymer Product.

| Tecophilic Typical Physical Test Data | | | | | |
|---|---|---|---|---|---|
| | ASTM | HP-60D-20 | HP-60D-35 | HP-60D-60 | HP-93A-100 |
| Durometer (Shore Hardness) | D2240 | 43D | 42D | 41D | 83A |
| Spec Gravity | D792 | 1.12 | 1.12 | 1.15 | 1.13 |
| Flex Modulus (psi) | D790 | 4,300 | 4,000 | 4,000 | 2,900 |
| Ultimate Tensile Dry (psi) | D412 | 8,900 | 7,800 | 8,300 | 2,200 |
| Ultimate Tensile Wet (psi) | D412 | 5,100 | 4,900 | 3,100 | 1,400 |
| Elongation Dry (%) | D412 | 430 | 450 | 500 | 1,040 |
| Elongation Wet (%) | D412 | 390 | 390 | 300 | 620 |

Figure 4:
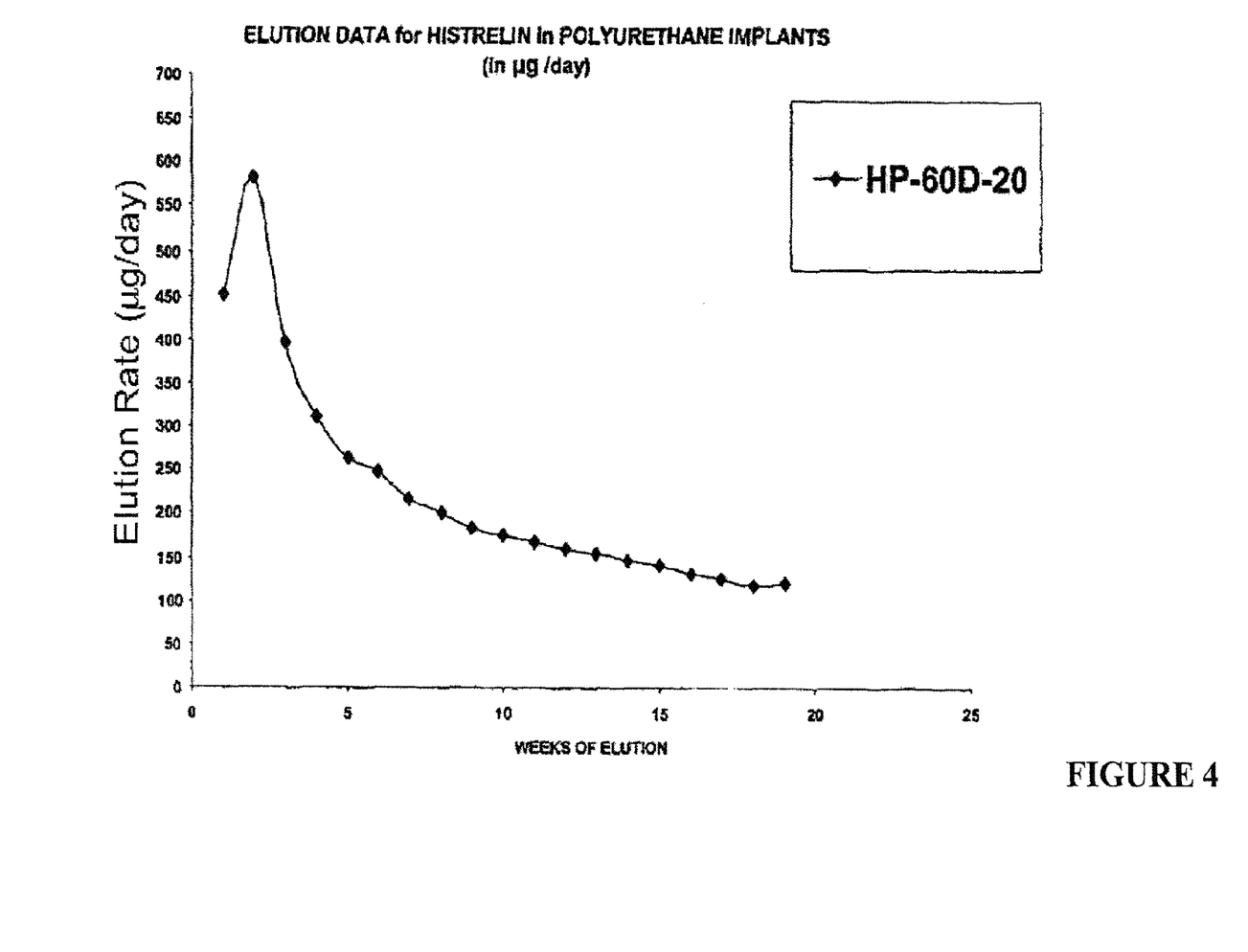
FIG. 4 is a graph of the elution rate of histrelin using an implant according to the present invention.

Hp-60D-20 is extruded to tubes with thickness of 0.30 mm with inside diameter of 1.75 mm. The tubes are then cut into 25 mm in length. One side of the tube is sealed with heat using a heat sealer. The sealing time is less than 1 minute. Four pellets of histrelin acetate are loaded into the tube. Each pellet weighs approximately 13.5 mg for a total of 54 mg. Each pellet is comprised of a mixture of 98% histrelin and 2% stearic acid. The second end open of the tube is sealed with heat in the same way as for the first end. The loaded implant is then conditioned and primed. The conditioning takes place at room temperature in a 0.9% saline solution for 1 day. Upon completion of the conditioning, the implant undergoes priming. The priming takes place at room temperatures in a 1.8% saline solution for 1 day. Each implant is tested in vitro in a medium selected to mimic the pH found in the human body. The temperature of the selected medium was kept at approximately 37° C. during the testing. The release rates are shown on FIG. 4.

| Histrelin elution rates | |
|---|---|
| WEEKS OF ELUTION | HP-60D-20 (µg/day) |
| 1 | 451.733 |
| 2 | 582.666 |
| 3 | 395.9 |
| 4 | 310.29 |
| 5 | 264.92 |
| 6 | 247.17 |
| 7 | 215.93 |
| 8 | 201.78 |
| 9 | 183.22 |
| 10 | 174.99 |
| 11 | 167.72 |
| 12 | 158.37 |
| 13 | 153.95 |
| 14 | 146.46 |
| 15 | 139.83 |
| 16 | 129.6 |
| 17 | 124.46 |
| 18 | 118.12 |
| 19 | 120.35 |

EXAMPLE 2

Figure 5:
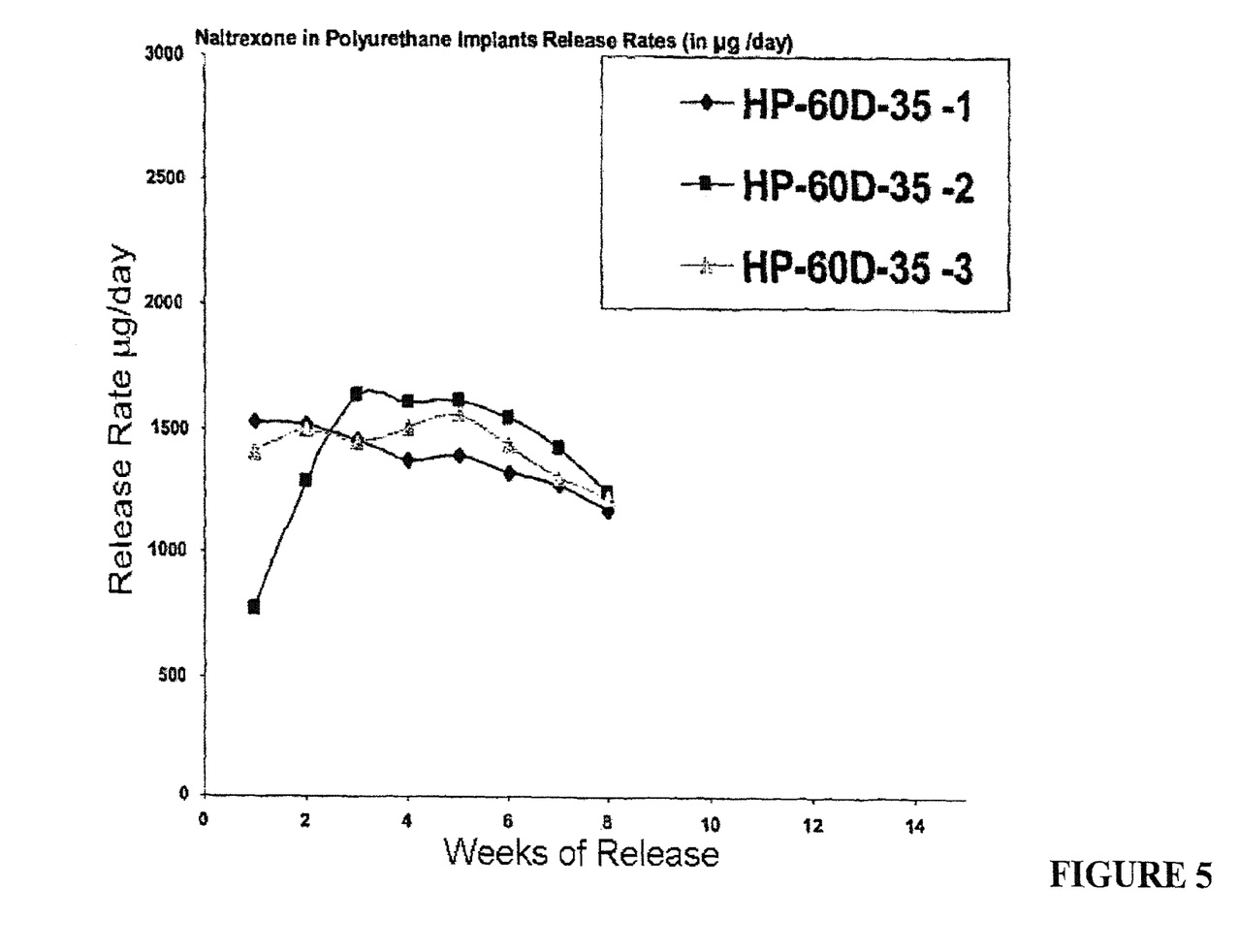
FIG. 5 is a graph of the elution rate of naltrexone using implants according to the present invention.

HP-60D-35 is extruded to tubes with thickness of 0.30 mm with inside diameter of 1.75 mm. The tubes are then cut into 32 mm in length. One side of the tube is sealed with heat using a heat sealer. The sealing time is less than 1 minute. Six pellets of naltrexone are loaded into the tubes and both open sides of the tubes are sealed with heat. Each pellet weighs approximately 15.0 mg for a total of 91 mg. The second end open of the tube is sealed with heat in the same way as for the first end. The loaded implant is then conditioned and primed. The conditioning takes place at room temperature in a 0.9% saline solution for 1 week. Upon completion of the conditioning, the implant undergoes priming. The priming takes place at room temperatures in a 1.8% saline solution for 1 week. Each implant is tested in vitro in a medium selected to mimic the pH found in the human body. The temperature of the selected medium was kept at approximately 37° C. during the testing. The release rates are shown on FIG. 5.

| Naltrexone elution rates | | | |
|---|---|---|---|
| WEEKS OF RELEASE | HP-60D-35-1 | HP-60D-35-2 | HP-60D-35-3 |
| 0 | (µg/day) | (µg/day) | (µg/day) |
| 1 | 1529.26 | 767.38 | 1400.95 |
| 2 | 1511.77 | 1280.03 | 1498.86 |
| 3 | 1456.01 | 1635.97 | 1449.49 |
| 4 | 1378.27 | 1607.13 | 1500.42 |
| 5 | 1393.05 | 1614.52 | 1558.37 |
| 6 | 1321.71 | 1550.39 | 1436.03 |
| 7 | 1273.07 | 1424.24 | 1300.73 |
| 8 | 1172.82 | 1246.48 | 1221.57 |

EXAMPLE 3

Figure 6:
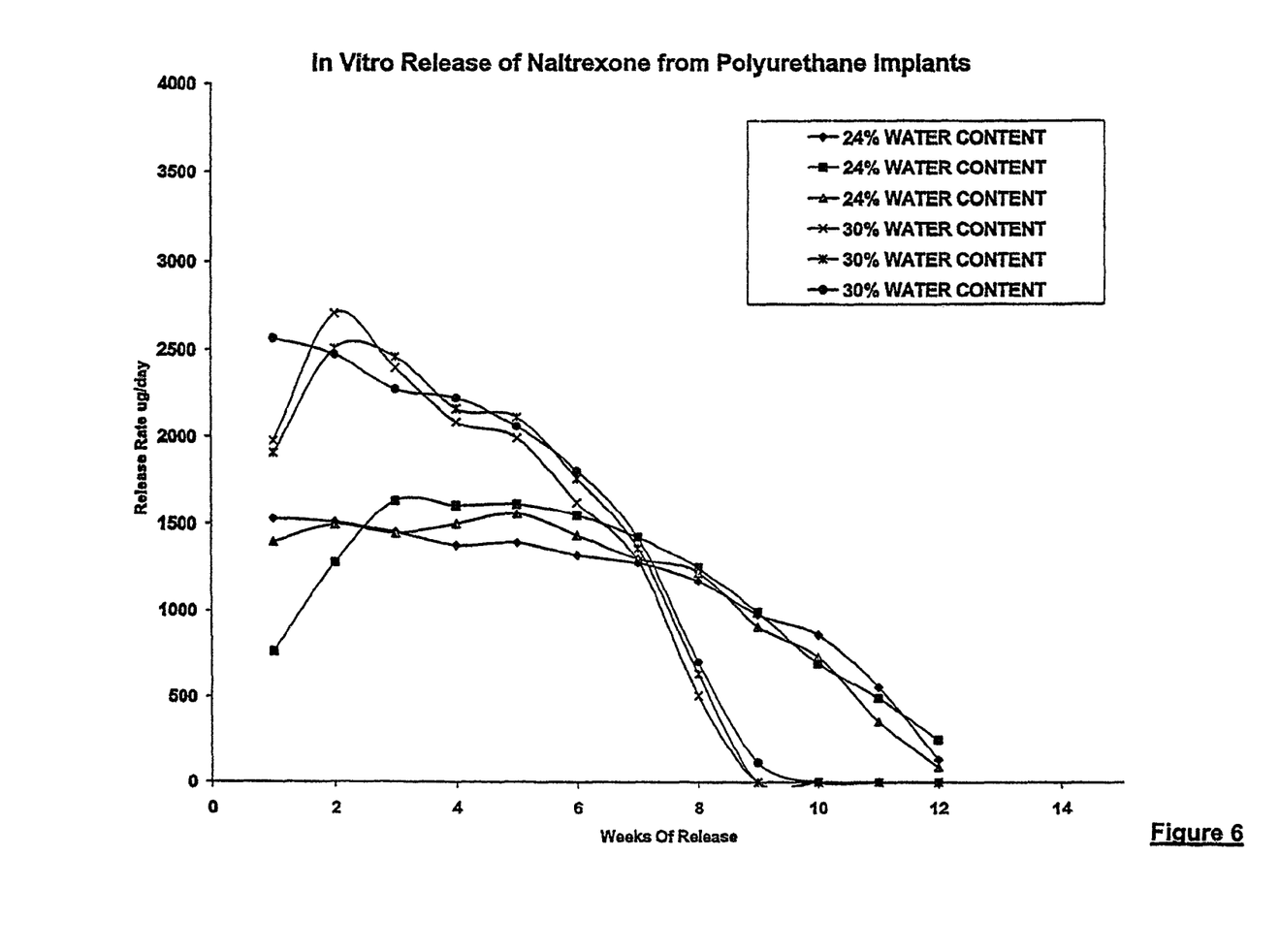
FIG. 6 is a graph of the elution rate of naltrexone from polyurethane implants according to the present invention.

In FIG. 6 there is a comparison of the release rates of naltrexone in vitro using two grades of polymer at two different water contents. Three runs were carried out and analyzed where the polymer of the implant had a water content of 24% and three runs were carried out where the polymer of the implant had a water content of 30%. The release rates were plotted against time. The polymer used for the runs at 24% water content was Tecophilic HP-60-D35 from Thermedics. The polymer used for the runs at 30% water content was Tecophilic HP-60-D60 from Thermedics. The data obtained in this example demonstrates the good reproducibility of the implants as prepared according to the present invention.

EXAMPLE 4

Figure 7:
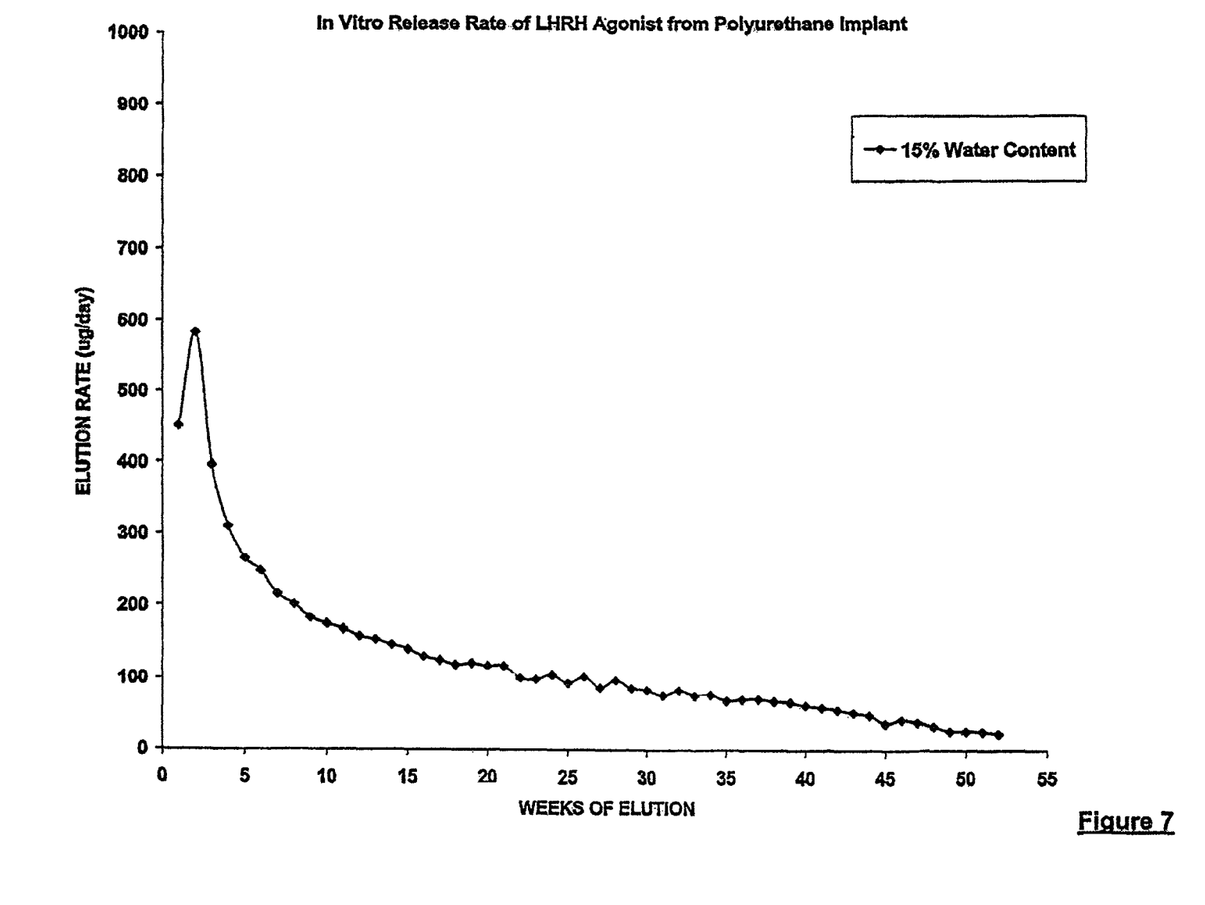
FIG. 7 is a graph of the elution rate of LHRH agonist (histrelin) from a polyurethane implant according to the present invention.

FIG. 7 shows a plot of the release rate of histrelin (LHRH Agonist) versus time. The polymer in this example had a water content of 15%. The polymer used was Tecophilic HP-60-D20 from Thermedics. The data points were taken weekly.

EXAMPLE 5

Figure 8:
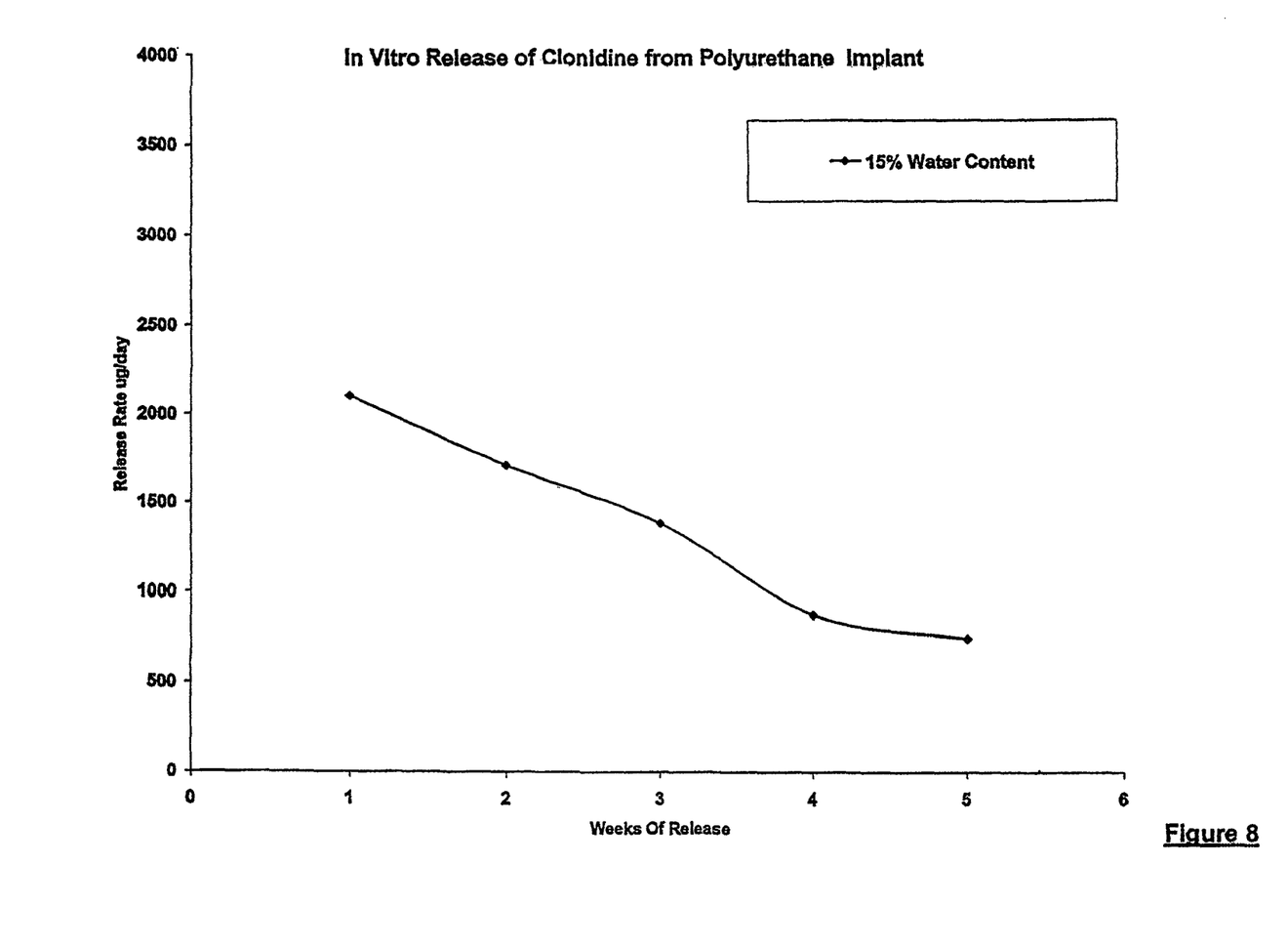
FIG. 8 is a graph of the elution rate of clonidine from a polyurethane implant according to the present invention.

FIG. 8 shows a plot of the release rate of clonidine versus time. The polymer in this example has a water content of 15%. The polymer used was Tecophilic BP-60-D20 from Thermedics. The data points were taken weekly.

What is claimed is:
1. An implantable drug delivery device for releasing one or more active ingredients at a substantially zero order rate in vitro by diffusion through a polyurethane based polymer for an extended period of time, said implantable drug delivery device comprising a polyurethane-based polymer configured to provide a cylindrically shaped reservoir, wherein the reservoir is sealed after being charged with an effective amount of a solid formulation comprising one or more active ingredients and wherein the one or more active ingredients and the polyurethane-based polymer are selected such that either: (i) both the one or more active ingredients and the polyurethane-based polymer exhibit hydrophilic characteristics, or (ii) both the one or more active ingredients and the polyurethane-based polymer exhibit hydrophobic characteristics, wherein the one or more active ingredients are selected from drugs that can act on the central nervous system, psychic energizers, tranquilizers, anti-convulsants, muscle relaxants, anti-parkinson, analgesic, anti-inflammatory, anesthetic, antispasmodic, muscle contractants, anti-microbials, anti-malarials, hormonal agents, sympathomimetic, cardiovascular, diuretics, and antiparasitic.

2. The implantable drug delivery device of claim 1, wherein the polyurethane based polymer is selected from the group consisting of thermoplastic polyurethane and thermoset polyurethane.

3. The implantable drug delivery device of claim 2, wherein the thermoplastic polyurethane comprises macrodiols, diisocyanates, difunctional chain extenders, or mixtures thereof.

4. The implantable drug delivery device of claim 2, wherein the thermoset polyurethane comprises multifunctional polyols, diisocyanates, chain extenders or mixtures thereof.

5. The implantable drug delivery device of claim 4, wherein the thermoset polyurethane comprises a polymer chain and cross-linking members, said thermoset polyurethane further including unsaturated bonds in the polymer chains and crosslinkers, initiators, or both as cross-linking members.

6. The implantable drug delivery device of claim 1, which is conditioned and primed under one or more parameters selected from the group consisting of time, temperature, and medium, and wherein the medium is selected to influence the desired delivery rates of the one or more active ingredients.

7. The implantable drug delivery device of claim 1, wherein the polyurethane comprises a hydrophilic pendant group selected from the group consisting of: ionic groups, carboxyl groups, ether groups, hydroxyl groups and mixtures of any two or more thereof.

8. The implantable drug delivery device of claim 1, wherein the one or more active ingredients and the polyurethane-based polymer are selected such that both the one or more active ingredients and the polyurethane-based polymer exhibit hydrophilic characteristics.

9. The implantable drug delivery device of claim 1, wherein the one or more active ingredients and the polyurethane-based polymer are selected such that both the one or more active ingredients and the polyurethane-based polymer exhibit hydrophobic characteristics.

10. The implantable drug delivery device of claim 1, wherein the solid formulation includes one or more pharmaceutically acceptable carriers that are not required for the substantially zero order release rate in vitro of the one or more active ingredients through the polyurethane-based polymer.

11. The implantable drug delivery device of claim 10, wherein the one or more pharmaceutically acceptable carriers are not required for the substantially zero order release rate in vitro of the one or more active ingredients as governed by Fick's Law of Diffusion.

12. An implantable drug delivery device for releasing one or more active ingredients at a substantially zero order rate in vitro by diffusion through a polyurethane-based polymer for a period of six weeks or more from the time of implantation, said implantable drug delivery device comprising a polyurethane-based polymer configured to provide a cylindrically shaped reservoir, wherein the reservoir is sealed after being charged with an effective amount of a solid formulation comprising one or more active ingredients exhibiting hydrophilic characteristics and the polyurethane-based polymer exhibits a percent equilibrium water content (% EWC) of about 30% or less, wherein the one or more active ingredients are selected from drugs that can act on the central nervous system, psychic energizers, tranquilizers, anti-convulsants, muscle relaxants, anti-parkinson, analgesic, anti-inflammatory, anesthetic, antispasmodic, muscle contractants, anti-microbials, anti-malarials, hormonal agents, sympathomimetic, cardiovascular, diuretics, and antiparasitic.

13. The implantable drug delivery device of claim 12, wherein the polyurethane-based polymer exhibits a % EWC ranging from about 15% to about 30%.

14. The implantable drug delivery device of claim 13, wherein the solid formation includes one or more pharmaceutically acceptable carriers that are not required for the substantially zero order release rate in vitro of the one or more active ingredients through the polyurethane-based polymer.

15. The implantable drug delivery device of claim 14, wherein the one or more pharmaceutically acceptable carriers are not required for the substantially zero order release rate in vitro of the one or more active ingredients as governed by Fick's Law of Diffusion.

16. The implantable drug delivery device of claim 14, wherein the solid formulation includes stearic acid.

17. A process for manufacturing a drug delivery device comprising selecting one or more active ingredients; selecting a polyurethane-based polymer formed as a hollow tube; loading a solid formulation comprising the one or more active ingredients into the tube; and sealing the tube; wherein the one or more active ingredients exhibit hydrophilic characteristics, and the polyurethane-based polymer exhibits a percent equilibrium water content (% EWC) of about 30% or less; and wherein the drug delivery device delivers the one or more active ingredients by diffusion through the polyurethane-based polymer at a substantially zero order release rate in vitro.

18. The process of claim 17, wherein the sealing of the hollow tube comprises inserting a pre-fabricated plug into an open end and applying heat or solvent to the pre-fabricated plug and polyurethane-based polymer.

19. The process of claim 17, wherein the sealing comprises inserting a pre-fabricated end plug at an open end of the hollow tube; applying an appropriate light-initiated and/or heat-initiated thermoset polyurethane formulation into an interface formed between the pre-fabricated end plug and the open end; and curing the polyurethane formulation with light and/or heat to seal the pre-fabricated plug in the end of the tube.

20. The process of claim 17 further comprising conditioning and priming comprises selecting a parameter selected from the group consisting of time, temperature, and medium to influence the substantially zero order release rate in vitro of the one or more active ingredients through the polyurethane-based polymer.

21. The process of claim 17, wherein the one or more active ingredients and the polyurethane-based polymer are selected such that both the one or more active ingredients and the polyurethane-based polymer exhibit hydrophilic characteristics.

22. The process of claim 17, wherein the solid formulation includes one or more pharmaceutically acceptable carriers that are not required for the substantially zero order release rate in vitro of the one or more active ingredients through the polyurethane-based polymer.

23. The process of claim 22, wherein the one or more pharmaceutically acceptable carriers are not required for the substantially zero order release rate in vitro of the one or more active ingredients as governed by Fick's Law of Diffusion.

24. The process of claim 17, wherein the hollow tube is formed by extrusion molding, injection molding, or spin-casting of the polyurethane-based polymer.

25. The process of claim 17, wherein the hollow tube is formed with two open ends.

26. The process of claim 17, wherein the hollow tube is formed with two open ends, and one end is sealed prior to the loading.

27. The process of claim 17, wherein the hollow tube is formed with one open end and one closed end.

28. The process of claim 17, wherein the one or more active ingredients are selected from drugs that can act on the central nervous system, psychic energizers, tranquilizers, anti-convulsants, muscle relaxants, anti-parkinson, analgesic, anti-inflammatory, anesthetic, antispasmodic, muscle contractants, anti-microbials, anti-malarials, hormonal agents, sympathomimetic, cardiovascular, diuretics, and antiparasitic.

29. An implantable drug delivery device for releasing one or more active ingredients at a substantially zero order rate in vitro by diffusion through a polyurethane based polymer for an extended period of time, said implantable drug delivery device comprising a polyurethane-based polymer configured to provide a cylindrically shaped reservoir, wherein the reservoir is sealed after being charged with an effective amount of a solid formulation comprising one or more active ingredients and wherein the one or more active ingredients and the polyurethane-based polymer are selected such that either: (i) both the one or more active ingredients and the polyurethane-based polymer exhibit hydrophilic characteristics, or (ii) both the one or more active ingredients and the polyurethane-based polymer exhibit hydrophobic characteristics, wherein the one or more active ingredients comprise histrelin or a pharmaceutically acceptable salt thereof.

30. The drug delivery device of claim 29, wherein the drug delivery device is conditioned and primed in an aqueous solution.

31. The drug delivery device of claim 29, wherein the solid formulation further comprises one or more pharmaceutically acceptable carriers.

32. The drug delivery device of claim 31, wherein the one or more pharmaceutically acceptable carriers comprise stearic acid.

* * * * *